(12) United States Patent
Cheng et al.

(10) Patent No.: US 10,406,569 B2
(45) Date of Patent: Sep. 10, 2019

(54) ATOMIZATION DEVICE AND CLEANING METHOD THEREOF

(71) Applicant: HCMed Innovations Co., LTD, Taipei (TW)

(72) Inventors: Chieh-Sheng Cheng, Taipei (TW); Wen-Yu Tsai, Taipei (TW)

(73) Assignee: HCMED INNOVATIONS CO., LTD, Taipei (TW)

( * ) Notice: Subject to any disclaimer, the term of this patent is extended or adjusted under 35 U.S.C. 154(b) by 226 days.

(21) Appl. No.: 15/423,570

(22) Filed: Feb. 2, 2017

(65) Prior Publication Data

US 2018/0065160 A1 Mar. 8, 2018

(30) Foreign Application Priority Data

Sep. 2, 2016 (TW) .............................. 105128452 A (51) Int. Cl.
| | | |
|---|---|---|
| *B08B 9/00* | (2006.01) | |
| *A61M 11/00* | (2006.01) | |
| *B05B 12/08* | (2006.01) | |
| *B05B 17/06* | (2006.01) | |
| *B05B 15/55* | (2018.01) | |
| *A61M 15/00* | (2006.01) | |

(52) U.S. Cl.
CPC ............. *B08B 9/00* (2013.01); *A61M 11/005* (2013.01); *A61M 15/0021* (2014.02); *A61M 15/0085* (2013.01); *B05B 12/081* (2013.01); *B05B 15/55* (2018.02); *B05B 17/0615* (2013.01); *A61M 2205/3386* (2013.01); *A61M 2205/3389* (2013.01)

(58) Field of Classification Search
CPC ............ A61M 11/005; A61M 15/0021; A61M 15/0085; A61M 2205/3386; A61M 2205/3389; B08B 9/00; B05B 12/081; B05B 15/55; B05B 17/0615
See application file for complete search history.

(56) References Cited

U.S. PATENT DOCUMENTS 6,769,626 B1 * 8/2004 Haveri ................. A61M 11/005
239/102.2
2010/0044460 A1 * 2/2010 Sauzade .............. B05B 17/0646
239/102.2

* cited by examiner

*Primary Examiner* — Douglas Lee
(74) *Attorney, Agent, or Firm* — Li & Cai Intellectual Property (USA) Office (57) ABSTRACT

An atomization device and a cleaning method thereof are provided. The atomization device includes a jar portion and a host device. The jar portion is movably assembled with the host device and includes a nozzle portion and a container portion. The nozzle portion communicates with the container portion and is provided with an atomizer disposed therein. The atomizer is coupled to the host device. The cleaning method includes the steps of: assembling the jar portion and the host device and turning on the host device; determining whether the container portion contains a liquid; entering a safe mode if the container portion does not contain the liquid or determining whether the nozzle portion contains the liquid if the container portion contains the liquid; and entering an atomization mode if the nozzle portion does not contain the liquid or entering a cleaning mode if the nozzle portion contains the liquid.

11 Claims, 8 Drawing Sheets

```
                    ┌─────────────────────┐
                    │ assembling the jar  │─ S601
                    │ portion and the     │
                    │ host device         │
                    └──────────┬──────────┘
                               ▼
                    ┌─────────────────────┐
                    │ immersing the jar   │─ S603
                    │ portion in the liquid│
                    └──────────┬──────────┘
                               ▼
                    ┌─────────────────────┐
                    │ turning on the host │─ S605
                    │ device              │
                    └──────────┬──────────┘
```

S611

┌──────────┐        ╱╲  S607
│entering a│  no   ╱  ╲
│safe mode │◄─────╱determining╲
└──────────┘      ╲whether the╱
                   ╲container╱
                    ╲portion╱
                     ╲contains╱
                      ╲a liquid╱
                       ╲yes╱
                        ▼

S613
┌──────────┐        ╱╲  S609
│entering an│ no   ╱determining╲
│atomization│◄────╱whether the ╲
│mode       │     ╲nozzle portion╱
└─────┬─────┘      ╲contains    ╱
      ▼             ╲the liquid╱
┌──────────────┐     ╲yes╱
│using the     │      ▼
│atomizer to   │   ┌─────────────────┐
│generate an   │   │entering a       │─ S617
│aerosol at a  │   │cleaning mode    │
│first resonant│   └────────┬────────┘
│frequency or  │            ▼                     S621
│in a first    │        ╱╲ S619              ┌──────────────┐
│direction     │       ╱determining╲   no    │using the     │
└──────────────┘       ╲whether the╱────────►│atomizer to   │
   S615                 ╲cleaning   ╱         │generate an   │
                         ╲mode has ╱          │aerosol at a  │
                          ╲exceeded╱          │second resonant│
                           ╲a pre- ╱          │frequency or   │
                            ╲determined╱       │in a second   │
                             ╲time period╱     │direction     │
                              ╲yes╱            └──────────────┘
                               ▼
                    ┌─────────────────────┐
                    │ stopping the cleaning│─ S623
                    │ mode and turning off │
                    │ the host device      │
                    └──────────┬──────────┘
                               ▼
                    ┌─────────────────────┐
                    │ turning off the      │─ S625
                    │ atomization device   │
                    └─────────────────────┘

FIG. 6

ATOMIZATION DEVICE AND CLEANING METHOD THEREOF

BACKGROUND

1. Technical Field

The present invention generally relates to an atomization device and a cleaning method thereof and, more particularly, to an atomization device and a cleaning method for cleaning the atomization device.

2. Description of Related Art

Atomization devices have been widely used in various applications such as temperature lowering, humidification, disinfection, dust suppression, medicine, and so on. Among them, for example, the particle sizes of the drugs for inhalation medical devices are no more than 3-5 µm, such that the drugs can reach the pulmonary alveoli and be absorbed directly by the human body to enhance the efficiency of drug actions. Moreover, for example, for the purpose of temperature lowering in a green house, the optimal atomized particle diameter is 17 µm because such atomized particles exhibit a moderate concentration to provide shading and significantly reduce the irrigation demand of the crops.

Presently, the vibrating atomization device uses a frequency-driven atomizer (i.e., a combination of a nozzle plate and a piezoelectric plate) to provide sonic oscillation and generate atomized particles. As the atomization device is used over time, the pores on the atomizer of the atomization device tend to be clogged with contaminations, fine particles or the like, which lowers the efficiency in generating fine atomized particles and causes inconvenience in the use of the atomization device.

SUMMARY

Accordingly, the present invention provides an atomization device and a cleaning method thereof to achieve improved convenience in the cleaning of the atomization device by determining whether a container portion and a nozzle portion contain a liquid.

The present invention provides a cleaning method for an atomization device. The atomization device includes a jar portion and a host device. The jar portion is movably assembled with the host device. The jar portion includes a nozzle portion and a container portion. The nozzle portion communicates with the container portion and is provided with an atomizer disposed therein. The atomizer is coupled to the host device. The cleaning method includes the steps of: assembling the jar portion and the host device and turning on the host device; determining whether the container portion contains a liquid; entering a safe mode if the container portion is determined to not contain the liquid or determining whether the nozzle portion contains the liquid if the container portion is determined to contain the liquid; and entering an atomization mode if the nozzle portion is determined to not contain the liquid or entering a cleaning mode if the nozzle portion is determined to contain the liquid.

The present invention provides an atomization device. The atomization device includes a jar portion and a host device. The jar portion includes a nozzle portion and a container portion. The nozzle portion communicates with the container portion and is provided with an atomizer disposed therein. The atomizer is coupled to the host device. The jar portion is movably assembled with the host device. The atomization device is cleaned using a cleaning method.

As previously stated, the present invention provides an atomization device capable of entering a cleaning mode to clean a nozzle portion and remove the contaminations that clog the nozzle portion to achieve improved convenience in the cleaning of the atomization device.

In order to further understand the techniques, means and effects of the present invention, the following detailed descriptions and appended drawings are hereby referred to, such that, and through which, the purposes, features and aspects of the present invention can be thoroughly and concretely appreciated; however, the appended drawings are merely provided for reference and illustration, without any intention to be used for limiting the present invention.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain the principles of the present invention.

DESCRIPTION OF THE EXEMPLARY EMBODIMENTS

The detailed description set forth below in connection with the appended drawings is intended as a description of certain embodiments of the present invention, and is not intended to represent the only forms that may be developed or utilized. The description sets forth the various functions in connection with the illustrated embodiments, but it is to be understood, however, that the same or equivalent functions may be accomplished by different embodiments that are also intended to be encompassed within the scope of the present invention.

Figure 1:
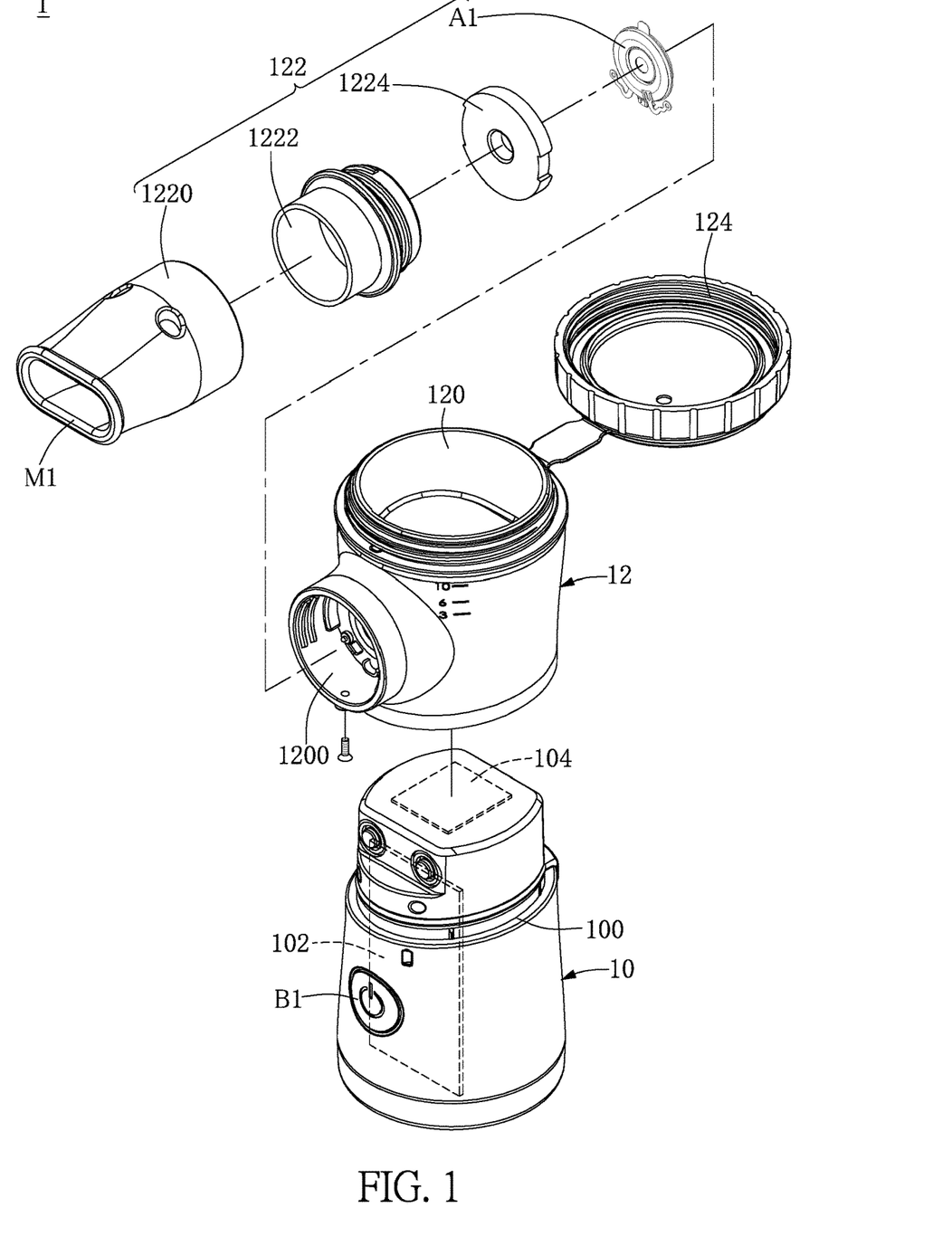
FIG. 1 is an exploded view of an atomization device according to one embodiment of the present invention.
Figure 1A:
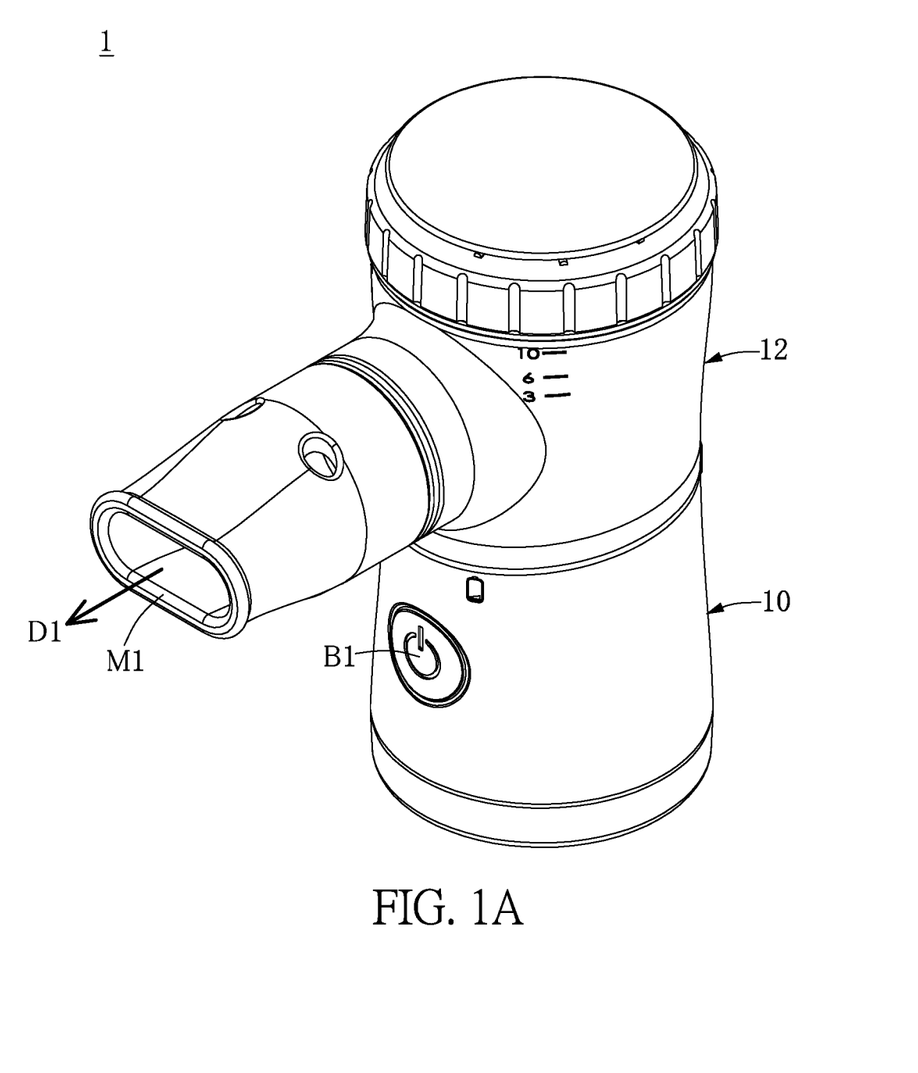
FIG. 1A is an assembled view of an atomization device according to one embodiment of the present invention.

FIG. 1 is an exploded view of an atomization device according to one embodiment of the present invention. FIG. 1A is an assembled view of an atomization device according to one embodiment of the present invention. Referring to FIG. 1 and FIG. 1A, an atomization device 1 includes a jar portion 12 and a host device 10. The jar portion 12 is movably disposed on the top of the host device 10. In practice, the atomization device 1 is, for example, a mouth/nasal spray gas or liquid gas device or an inhalation medical device. The vibrating atomization device 1 provides sonic oscillation to generate atomized particles using the frequency driven atomizer A1 (i.e., a combination of a nozzle plate and a piezoelectric plate). However, the present invention is not limited to the previous example of the atomizer A1 in the present embodiment.

The jar portion 12 contains liquid medicine or other liquids such as distilled water, physiological saline, artificial tears, and so on. The user may design the type and the shape of the jar portion 12 according to practical demands. The present invention is not limited to the previous example of the jar portion 12.

More particularly, the jar portion 12 includes a container portion 120, a nozzle portion 122 and a cap 124. In practice, the container portion 120 includes a port 1200 to communicate with the nozzle portion 122. The nozzle portion 122 includes a nozzle member 1220, a rotation member 1222, a buffer member 1224 and an atomizer A1. In other embodiments, the nozzle portion 122 may not include the nozzle member 1220 or the buffer member 1224. The present invention is not limited to the previous example of the nozzle portion 122.

The buffer member 1224 (made of, for example, resilient plastics or resilient rubber) is removably disposed in the port 1200 and against the atomizer A1. The rotation member 1222 is rotatably and removably disposed on the port 1200 and against the buffer member 1224. The nozzle member 1220 is removably disposed on the rotation member 1222.

The host device 10 is configured to generate a vibrating frequency to drive the atomizer A1 such that the atomizer A1 provides sonic oscillation to generate atomized particles. The sonic oscillation also includes ultrasonic oscillation. The oscillation frequency includes the sonic band (<20 KHz) and the ultrasonic band (≥20 KHz). For example, the user can press the switch button B1 on the host device 10 to turn on the atomization device 1 to provide sonic oscillation such that the atomization device 1 outputs 3-5 μm atomized drug particles along a first direction D1 to effectively reach the pulmonary alveoli and be directly absorbed by the human body. Moreover, the user can press the switch button B1 on the host device 10 again to stop the atomization device 1 from providing sonic oscillation. The first direction D1 indicates the direction from the container portion 120 to the nozzle M1 of the nozzle portion 122. The present invention is not limited to the previous example of the atomization device 1.

The host device 10 includes a structural body 100 and a circuit board 102. In practice, the circuit board 102 is disposed in the structural body 100. The structural body 100 is, for example, a structure, a framework or a housing being provided with at least one battery and one circuit board 102 disposed therein. The circuit board 102 is, for example, a printed circuit board, a flexible circuit board or other circuit boards. The circuit board 102 is designed with an atomization circuit, an ultrasonic oscillation generation circuit, a sonic oscillation generation and control circuit or a combination thereof. The circuit board 102 is coupled to the atomizer A1. The present invention is not limited to the previous examples of the structural body 100 and the circuit board 102.

Moreover, the host device 10 further includes a sensor unit 104 disposed on the structural body 100, on the jar portion 12 or anywhere on the atomization device 1. The sensor unit 104 senses the amount of the liquid in the jar portion 12 contactly or non-contactly. When the sensor unit 104 determines that the jar portion 12 does not contain the liquid, the sensor unit 104 transmits a sensed signal to the host device 10. The sensed signal indicates that the host device 10 is to be turned off. Otherwise, when the sensor unit 104 determines that the jar portion 12 contains a liquid, the sensor unit 104 transmits another sensed signal to the host device 10.

The sensor unit 104 is, for example, a water level sensor that senses the amount of the liquid in the jar portion 12 contactly or non-contactly and outputs the sensed signal to a control unit (not shown) on the circuit board 102 in the host device 10 so as to prevent the sonic oscillation circuit or the sonic oscillator in the atomization device 1 from idling. The sensor unit 104 is, for example, a water level sensor disposed in the jar portion 12, or disposed on the structural body 100 of the host device 10 outside the jar portion 12. The water level sensor disposed in the jar portion 12 is, for example, a contact water level sensor. The water level sensor disposed on the structural body 100 is, for example, a non-contact water level sensor. The present invention is not limited to the previous example of the sensor unit 104 and where the sensor unit 104 is disposed.

For example, the sensor unit 104 senses the amount of the liquid in the jar portion 12 non-contactly. The sensor unit 104 is disposed on structural body 100 or on the circuit board 102. In other words, the sensor unit 104 is not disposed in the jar portion 12 containing the liquid or the liquid medicine therein. Therefore, the sensor unit 104 senses the amount of the liquid in the jar portion 12 non-contactly and transmits a sensed signal to the control unit in the host device 10. When the sensed signal conforms to a first pre-determined value of the control unit in the host device 10, the sensor unit 104 determines that the jar portion 12 does not contain the liquid.

In practice, the non-contact sensor unit 104 is implemented using, for example, an antenna (not shown), a clamp circuit (not shown) and a voltage-divider circuit (not shown) or a combination thereof. The clamp circuit is electrically connected to the antenna and the voltage-divider circuit. The voltage-divider circuit is electrically connected to a control unit. The sensed signal is a voltage waveform, a peak-to-peak voltage value Vpp or other voltage values of a voltage waveform indicating the amount of the liquid in the jar portion 12. As the voltage waveform conforms to the first pre-determined value, the control unit in the host device 10 is turned off. Moreover, as another voltage waveform exceeds the first pre-determined value of the host device 10, the sensor unit 104 determines that the jar portion 12 contains a liquid therein.

For example, the voltage waveform includes, for example, at least one peak-to-peak voltage value (Vpp). The first pre-determined value is, for example, a pre-determined peak-to-peak voltage value. When the actual sensed voltage waveform is larger than or exceeds the pre-determined peak-to-peak voltage value, the control unit is activated such that the control unit controls the sonic oscillation provided by the atomization device 1. When the amount of the liquid in the jar portion 12 drops to zero (i.e., the actual sensed voltage waveform is smaller than or equal to the pre-determined peak-to-peak voltage value), the control unit is turned off. Accordingly, the atomization device 1 stops.

In other embodiments, the first pre-determined value is, for example, a voltage value, an average voltage value, a root mean square (RMS) voltage value or other values. A person with ordinary skill in the art may freely design the first pre-determined value according to the spirits of the present embodiment.

For example, the user may pour a certain amount of liquid medicine into the jar portion 12 and press the switch button B1 to turn on the atomization device 1. The sensor unit 104 senses the level of the liquid in the jar portion 12 such that the sensor unit 104 outputs a sensed signal with a voltage waveform having larger amplitude to the control unit. Therefore, the control unit is to be turned on. Before the level of the liquid in the jar portion 12 drops to zero, the sensor unit 104 outputs a sensed signal with a voltage waveform having medium amplitude to the control unit. Therefore, the control unit continues conducting the sonic oscillation. The voltage waveform having larger amplitude changes with the level of the liquid and gradually becomes a voltage waveform having medium or smaller amplitude.

When the level of the liquid in the jar portion 12 drops to zero, the sensor unit 104 outputs a sensed signal with a voltage waveform having smaller amplitude to the control unit. The voltage waveform having smaller amplitude has, for example, a smaller peak-to-peak voltage value. When the control unit determines that the peak-to-peak voltage value conforms to a first pre-determined value, the control unit turns off the atomization device 1. In other words, the sensed signal with a voltage waveform having a larger amplitude indicates that the host device 10 may be turned on or continue to work. The sensed signal with a voltage waveform having smaller amplitude indicates that the host device 10 is to be turned off.

Figure 2:
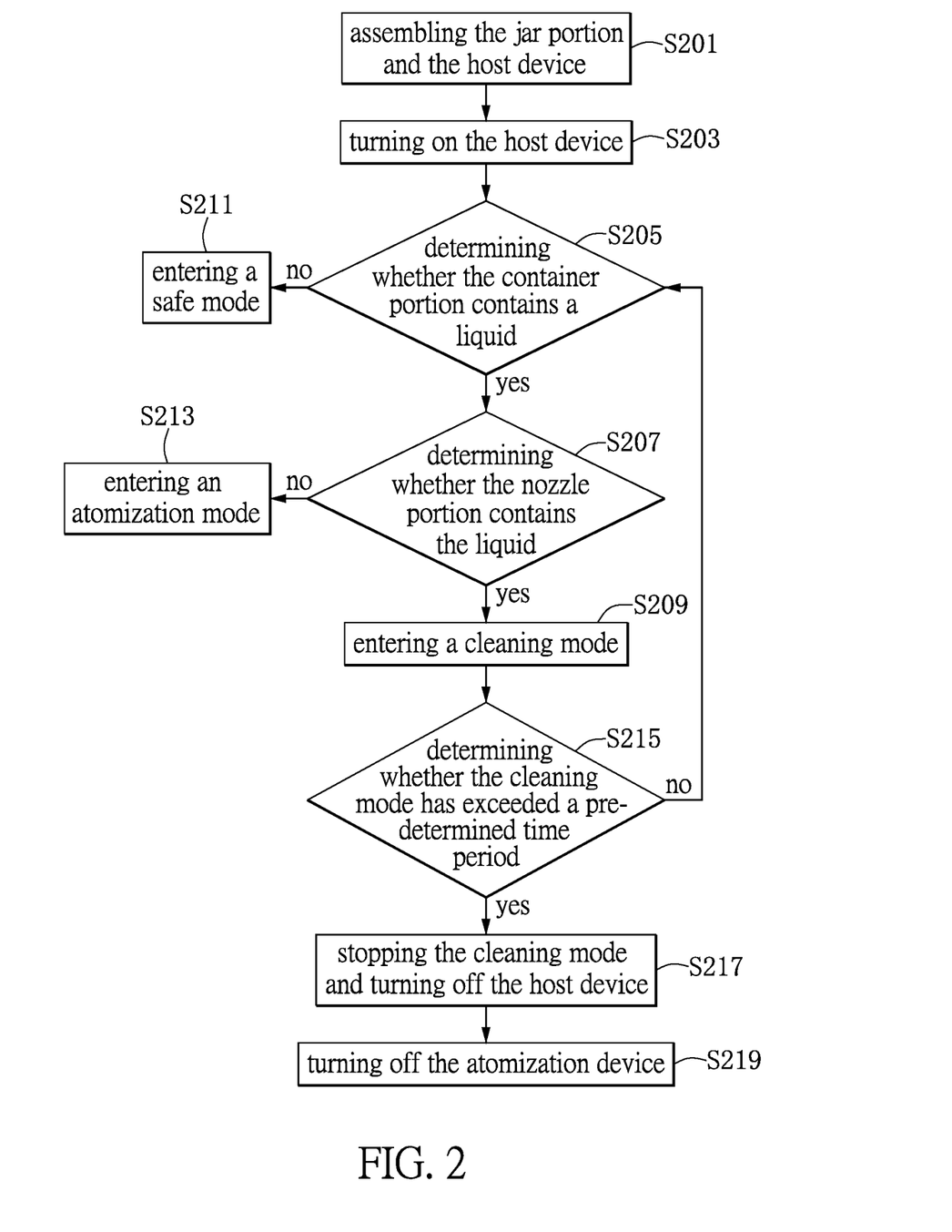
FIG. 2 is a flowchart of a cleaning method of an atomization device according to one embodiment of the present invention.

FIG. 2 is a flowchart of a cleaning method of an atomization device according to one embodiment of the present invention. Referring to FIG. 2, the cleaning method is applicable to the atomization device 1. The atomization device 1 includes a jar portion 12 and a host device 10. The jar portion 12 is movably assembled with the host device 10. The jar portion 12 includes a nozzle portion 122 and a container portion 120. The nozzle portion 122 communicates with the container portion 120 and is provided with an atomizer A1 disposed therein. The atomizer A1 is coupled to the host device 10. The cleaning method includes the steps herein.

In Step S201, the jar portion 12 and the host device 10 are assembled. In practice, after the jar portion 12 and the host device 10 are assembled, the atomization device 1 is formed. In Step S203, the host device 10 is turned on. Therefore, the atomization device 1 starts to work. Afterwards, in Step S205, whether the container portion 120 contains a liquid is determined. In practice, the container portion 120 in the jar portion 12 contains liquid medicine. The host device 10 uses the sensor unit 104 to determine whether the container portion 120 contains a liquid. If, in Step S205, the container portion 120 is determined to not contain the liquid, Step S211 is performed to enter a safe mode. The safe mode indicates, for example, turning off the host device 10.

If, in Step S205, the container portion 120 is determined to contain the liquid, Step S207 is performed to determine whether the nozzle portion 122 contains the liquid. If, in Step S207, the nozzle portion 122 is determined to not contain the liquid, Step S213 is performed to enter an atomization mode. In practice, the atomization mode indicates that the liquid medicine in the container portion 120 passes the atomizer A1 to form an aerosol. In other words, the atomization device 1 enters an atomization mode when the container portion 120 contains the liquid and the nozzle portion 122 does not contain the liquid.

Then, if, in Step S207, the nozzle portion 122 is determined to contain the liquid, Step S209 is performed to enter a cleaning mode. In practice, the cleaning mode indicates that the atomization device 1 automatically sucks a detergent from the outside through the nozzle portion 122 and removes the contaminations clogging the pores on the atomizer A1. In brief, the contaminations clogging the pores on the atomizer A1 are removed in the cleaning mode so as to clean the atomizer A1.

Afterwards, in Step S215, whether the cleaning mode has exceeded a pre-determined time period is determined. If, in Step S215, the cleaning mode is determined to have exceeded a pre-determined time period, Step S217 is performed to stop the cleaning mode and turn off the host device 10. In Step S219, the atomization device 1 is turned off. In practice, the pre-determined time period is, for example, one minute, five minutes or any other time periods. For convenience, the pre-determined time period in the present embodiment is exemplified by five minutes. In other words, the atomization device 1 is turned off automatically after the atomization device 1 has entered the cleaning mode for five minutes.

If, in Step S215, the cleaning mode is determined to have not exceeded the pre-determined time period, Step S205 is performed. In practice, everything after Step S205 has been described as above. If the container portion 120 of the atomization device 1 does not contain the liquid and the user interrupts the cleaning mode and starts to use the atomization device 1 before the cleaning mode has completed the pre-determined time period (for example, only one minute in the pre-determined five-minute cleaning mode has passed), Step S211 is performed. In other words, when the cleaning mode is interrupted before it has completed the pre-determined time period, the atomization device 1 enters the safe mode to prevent the atomization device 1 from idling.

As previously stated, in the present embodiment, whether the atomization device 1 enters the cleaning mode is determined by determining whether both the container portion 120 and the nozzle portion 122 contain the liquid. When both the container portion 120 and the nozzle portion 122 contain the liquid, the atomization device 1 enters the cleaning mode. When the container portion 120 is determined to contain the liquid and the nozzle portion 122 is determined to not contain the liquid, the atomization device 1 enters the atomization mode. When the container portion 120 is determined to not contain the liquid, the atomization device 1 enters the safe mode. The present invention is not limited to the previous example of the cleaning method.

Figure 3:
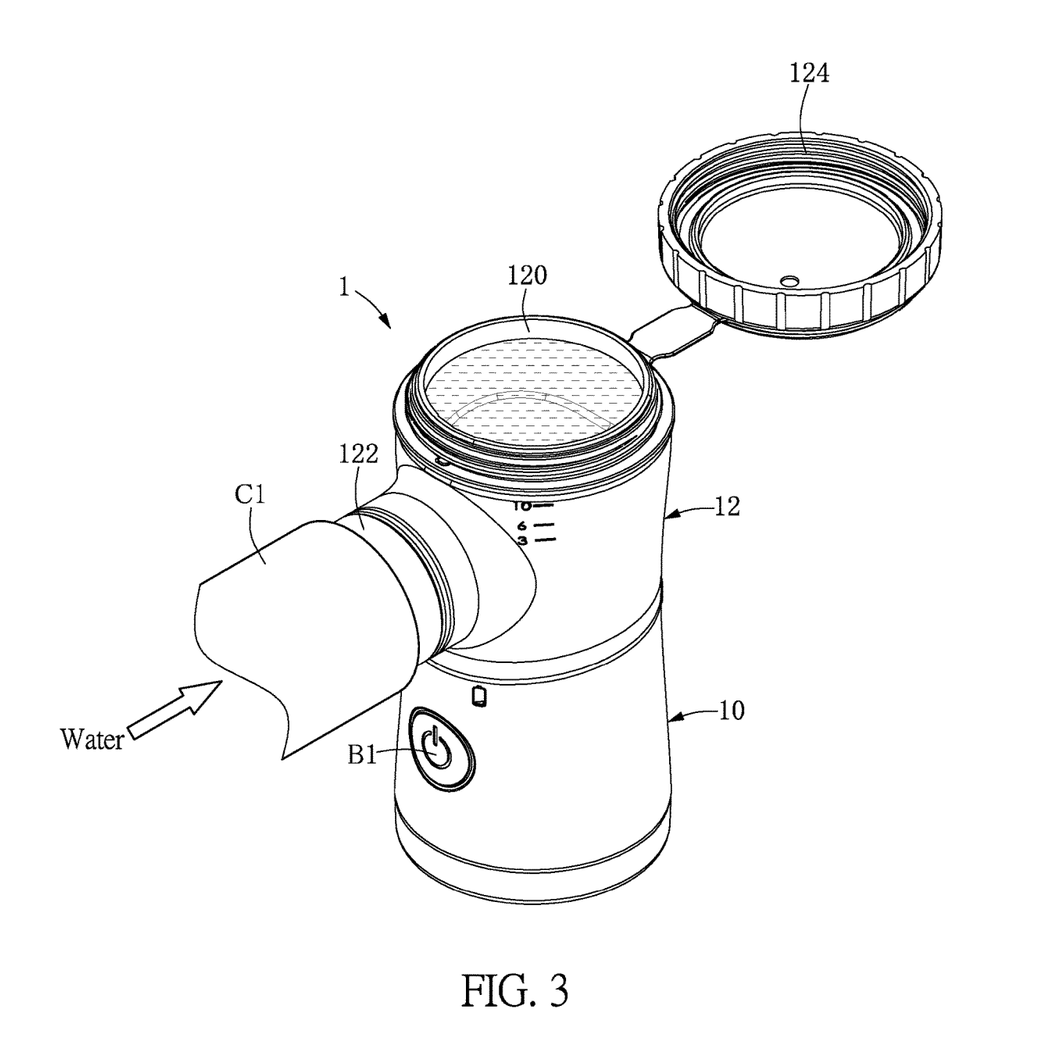
FIG. 3 is a schematic diagram showing the operation of an atomization device according to one embodiment of the present invention.

FIG. 3 is a schematic diagram showing the operation of an atomization device according to one embodiment of the present invention. Referring to FIG. 3, the nozzle portion 122 is connected to a communication pipe C1. Both the communication pipe C1 and the container portion 120 contain the liquid. In other words, in FIG. 3, when the user presses the switch button B1, the atomization device 1 enters the cleaning mode to remove the contaminations clogging the pores on the atomizer A1.

Figure 4:
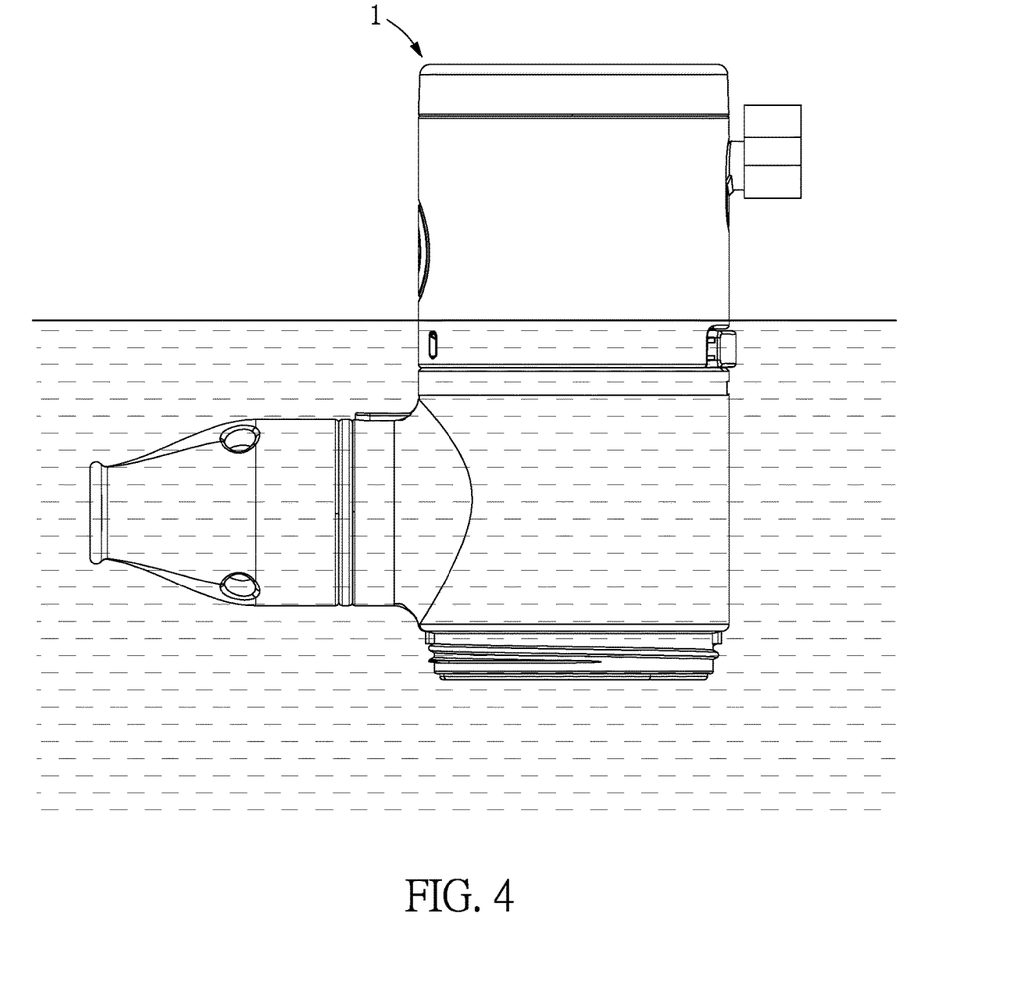
FIG. 4 is a schematic diagram showing the operation of an atomization device according to another embodiment of the present invention.

FIG. 4 is a schematic diagram showing the operation of an atomization device according to another embodiment of the present invention. Referring to FIG. 4, the jar portion 12 of the atomization device 1 is immersed into a liquid such that both the nozzle portion 122 and the container portion 120 contain the liquid. Therefore, in FIG. 4, when the user presses the switch button B1, the atomization device 1 enters the cleaning mode to remove the contaminations clogging the pores on the atomizer A1. In other embodiments, the atomization device 1 may be immersed into the liquid completely, vertically, or inclinedly. The atomization device 1 may be a water-proof device. When the user presses the switch button B1, the atomization device 1 enters the cleaning mode.

Moreover, FIG. 4 illustrates the operation of the atomization device 1 in the cleaning mode without the cap 124. In other embodiments, the atomization device 1 may enter the cleaning mode with the cap 124 on the jar portion 12. Moreover, FIG. 4 illustrates the operation of the atomization device 1 in the cleaning mode with the nozzle member 1220. In other embodiments, the user may remove the nozzle member 1220 and enter the cleaning mode as in FIG. 4. The present invention is not limited to the previous examples of how the atomization device 1 operates.

Figure 5:
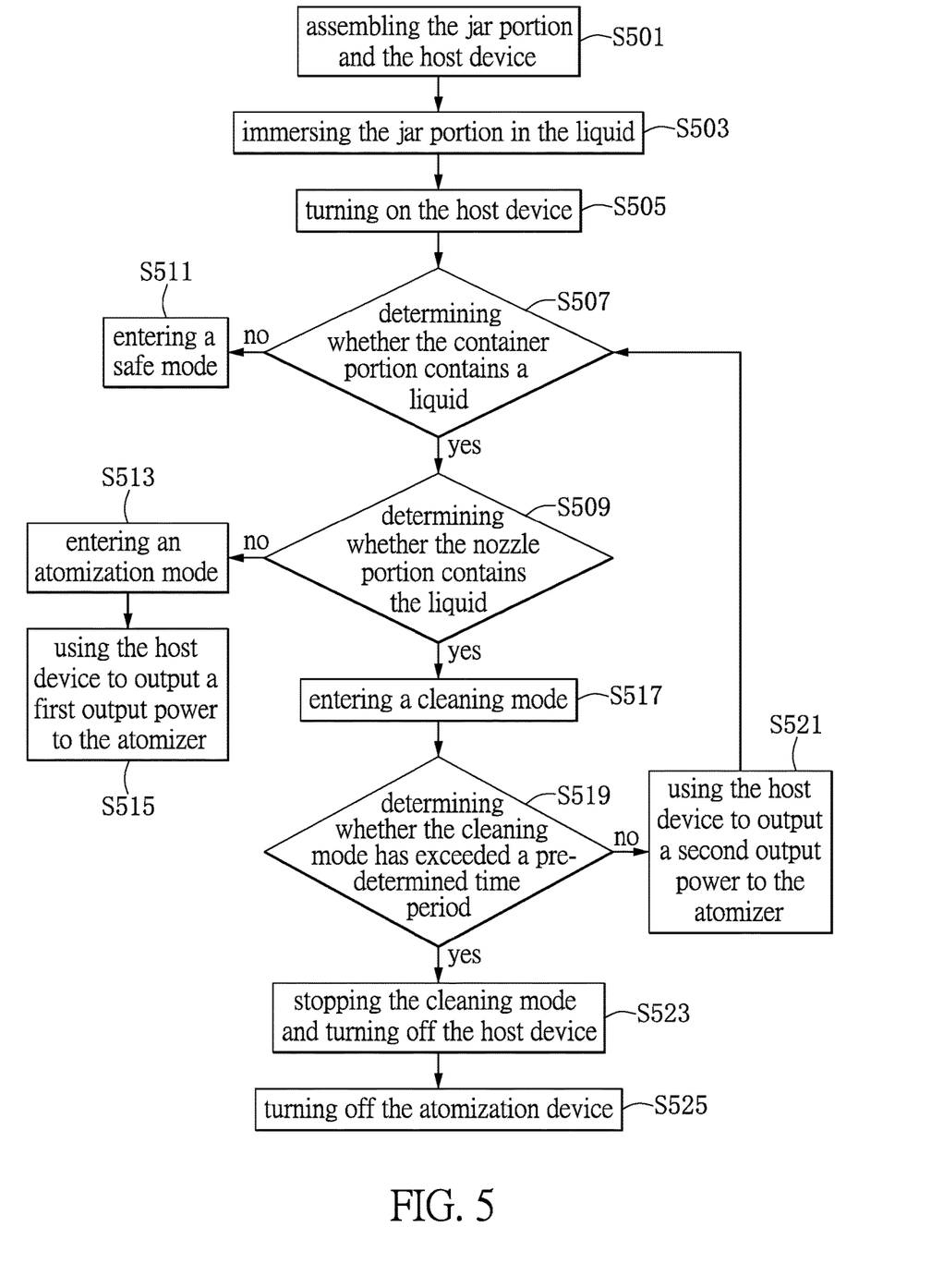
FIG. 5 is a flowchart of a cleaning method of an atomization device according to another embodiment of the present invention.

FIG. 5 is a flowchart of a cleaning method of an atomization device according to another embodiment of the present invention. Referring to FIG. 5, the cleaning method is applicable to the atomization device 1. The cleaning method includes the steps herein.

In Step S501, the jar portion 12 and the host device 10 are assembled. In Step S503, the jar portion 12 is immersed into the liquid as shown in FIG. 4. In Step S505, the host device 10 is turned on. In Step S507, whether the container portion 120 contains the liquid is determined. If, in Step S507, the container portion 120 is determined to contain the liquid, Step S509 is performed to determine whether the nozzle portion 122 contains the liquid. If, in Step S507, the container portion 120 is determined to not contain the liquid, Step S511 is performed to enter a safe mode.

In Step S509, whether the nozzle portion 122 contains the liquid is determined. If, in Step S509, the nozzle portion 122 is determined to not contain the liquid, Step S513 is performed to enter an atomization mode. In Step S515, the host device 10 outputs a first output power to the atomizer A1. If, in Step S509, the nozzle portion 122 is determined to contain the liquid, Step S517 is performed to enter a cleaning mode.

Afterwards, in Step S519, whether the cleaning mode has exceeded a pre-determined time period is determined. If, in Step S519, the cleaning mode is determined to have not exceeded the pre-determined time period, Step S521 is performed to use the host device 10 to output a second output power to the atomizer A1. The second output power is higher than the first output power. In other words, the atomization device 1 enters the cleaning mode with a higher output power so as to remove the contaminations clogging the pores on the atomizer A1.

For example, in the atomization mode, the atomization device 1 outputs, for example, 10-W output power to drive the atomizer A1 to provide sonic oscillation. Therefore, as time goes by, the pores on the atomizer A1 are clogged by the contaminations in the liquid. Therefore, in the cleaning mode, the atomization device 1 outputs, for example, 20-W output power to drive the atomizer A1 to provide sonic oscillation. Therefore, the atomizer A1 increases the oscillation intensity or the oscillation frequency to remove the contaminations clogging the pores on the atomizer A1 with the use of a detergent. In brief, in the present embodiment, the output power of the atomization device 1 is enhanced to remove the contaminations clogging the pores on the atomizer A1.

If, in Step S519, the cleaning mode is determined to have exceeded the pre-determined time period, Step S523 is performed to stop the cleaning mode and turn off the host device 10. In Step S525, the atomization device 1 is turned off.

Figure 5A:
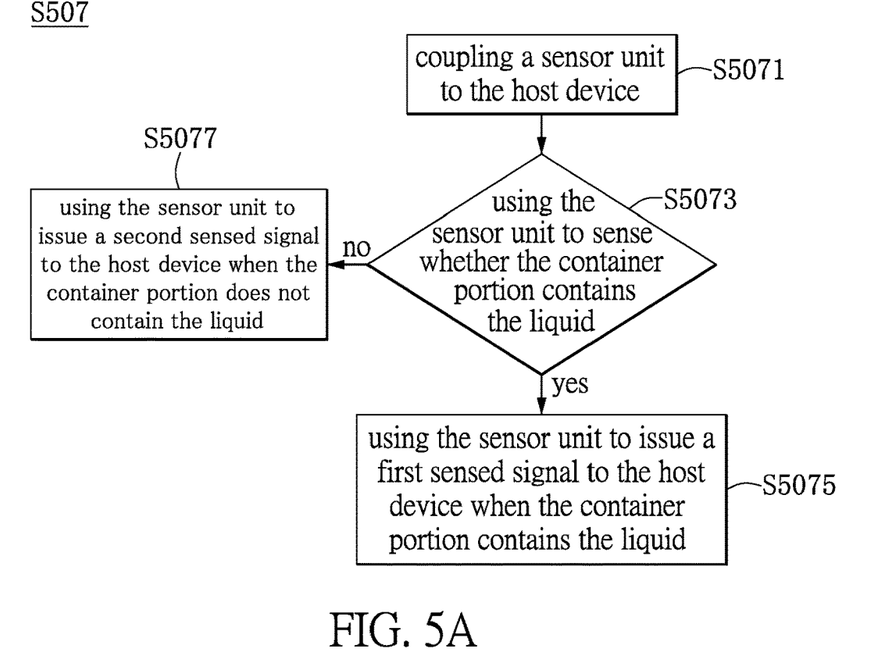
FIG. 5A is a flowchart of a cleaning method of an atomization device according to still another embodiment of the present invention.

FIG. 5A is a flowchart of a cleaning method of an atomization device according to still another embodiment of the present invention. Referring to FIG. 5A, Step S507 in FIG. 5 will be further described in detail herein. Step S507 is similar to Step S205 in FIG. 2. In practice, Step S507 includes the steps as follows.

In Step S5071, the sensor unit 104 is coupled to the host device 10. The sensor unit 104 is implemented using a contact sensor, a weight sensor, a water level sensor or a non-contact sensor. In other words, the sensor unit 104 is capable of determining whether the container portion 120 contains a liquid therein.

In Step S5073, the sensor unit 104 senses whether the container portion 120 contains the liquid. If, in Step S5073, the container portion 120 is determined to contain the liquid, Step S5075 is performed such that the sensor unit 104 issues a first sensed signal to the host device 10 when the container portion 120 contains the liquid. On the contrary, if, in Step S5073, the container portion 120 is determined to not contain the liquid, Step S5077 is performed such that the sensor unit 104 issues a second sensed signal to the host device 10 when the container portion 120 does not contain the liquid.

For example, the first sensed signal and the second sensed signal are, for example, sensed water level signals, respectively. When the jar portion 12 contains the liquid therein, the atomization device 1 generates a sensed signal with a voltage waveform having larger amplitude. Therefore, the sensor unit 104 senses that the jar portion 12 contains the liquid therein. On the contrary, when the jar portion 12 does not contain the liquid therein, the atomization device 1 generates a sensed signal with a voltage waveform having smaller amplitude. Therefore, the sensor unit 104 senses that the jar portion 12 does not contain the liquid therein. Accordingly, the atomization device 1 uses the sensor unit 104 to sense whether the container portion 120 of the jar portion 12 contains the liquid therein. The present invention is not limited to the details of Step S507.

Figure 5B:
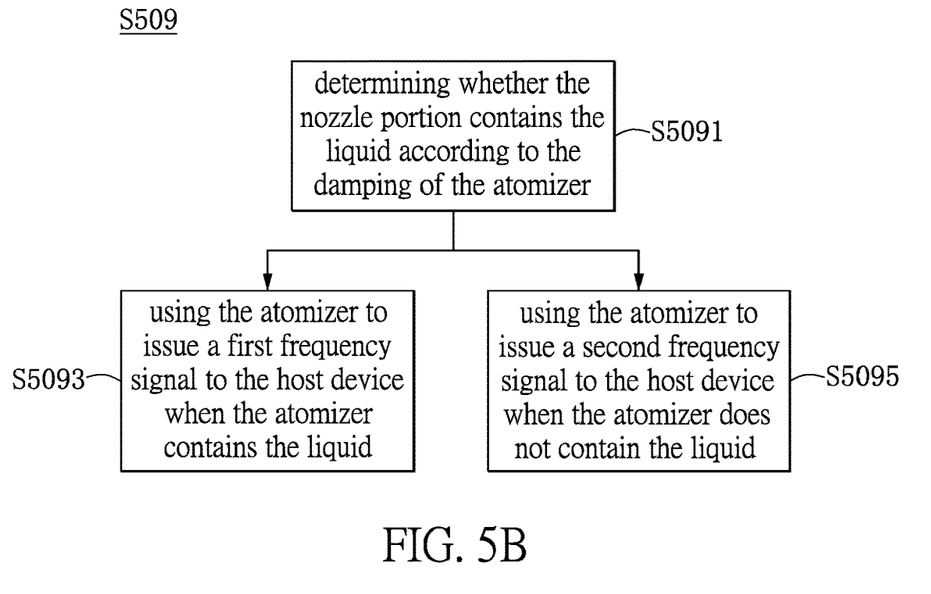
FIG. 5B is a flowchart of a cleaning method of an atomization device according to still another embodiment of the present invention.

FIG. 5B is a flowchart of a cleaning method of an atomization device according to still another embodiment of the present invention. Referring to FIG. 5B, Step S509 in FIG. 5 will be further described in detail herein. Step S509 is similar to Step S207 in FIG. 2. In practice, Step S509 includes the steps as follows.

In Step S5091, whether the nozzle portion 122 contains the liquid is determined according to the damping of the atomizer A1. In practice, the atomizer A1 (i.e., a piezoelectric plate) has high sensitivity. Therefore, in the present embodiment, whether the nozzle portion 122 contains the liquid is determined according to the resonant frequency signal transmitted by the atomizer A1.

When the liquid exists in the atomizer A1, the damping of the atomizer A1 is higher. Therefore, the sensor unit 104 senses a lower resonant frequency. On the contrary, when the atomizer A1 does not contain any liquid, the damping of the atomizer A1 becomes lower. Therefore, the sensor unit 104 senses a higher resonant frequency. Accordingly, in the present embodiment, whether the nozzle portion 122 contains the liquid is determined according to the sensed resonant frequency.

More particularly, in Step S5093, when the atomizer A1 contains the liquid, the atomizer A1 issues a first frequency signal to the host device 10. In Step S5095, when the atomizer A1 does not contain the liquid, the atomizer A1 issues a second frequency signal to the host device 10. The second frequency is higher than the first frequency.

In other words, when the nozzle portion 122 contains the liquid therein, the atomizer A1 issues a first frequency signal with a lower resonant frequency to the host device 10 such that the host device 10 determines that the nozzle portion 122 contains the liquid therein. On the contrary, when the nozzle portion 122 does not contain the liquid therein, the atomizer A1 issues a second frequency signal with a higher resonant frequency to the host device 10 such that the host device 10 determines that the nozzle portion 122 does not contain the liquid therein. The present invention is not limited to the details of Step S509.

Figure 6:
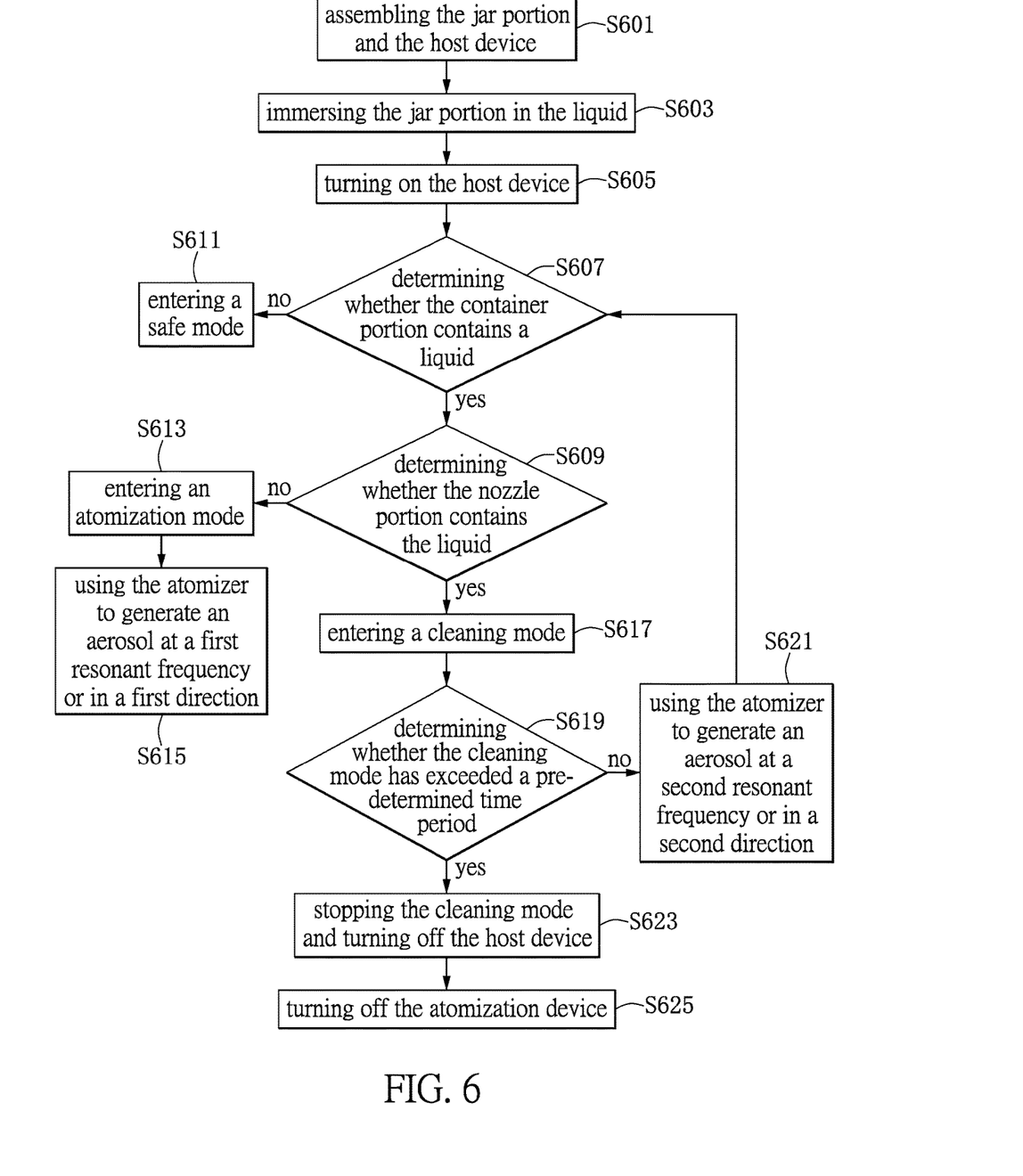
FIG. 6 is a flowchart of a cleaning method of an atomization device according to still another embodiment of the present invention.

FIG. 6 is a flowchart of a cleaning method of an atomization device according to still another embodiment of the present invention. Referring to FIG. 6, the cleaning method is applicable to the atomization device 1. The cleaning method includes the steps herein.

In Step S601, the jar portion 12 and the host device 10 are assembled. In Step S603, the jar portion 12 is immersed into the liquid as shown in FIG. 4. In Step S605, the host device 10 is turned on. In Step S607, whether the container portion 120 contains the liquid is determined. If, in Step S607, the container portion 120 is determined to contain the liquid, Step S609 is performed to determine whether the nozzle portion 122 contains the liquid. If, in Step S607, the container portion 120 is determined to not contain the liquid, Step S611 is performed to enter a safe mode.

In Step S609, whether the nozzle portion 122 contains the liquid is determined. If, in Step S609, the nozzle portion 122 is determined to not contain the liquid, Step S613 is performed to enter an atomization mode. In Step S615, the atomizer A1 generates an aerosol at a first resonant frequency or in a first direction D1. If, in Step S609, the nozzle portion 122 is determined to contain the liquid, Step S617 is performed to enter a cleaning mode.

Afterwards, in Step S619, whether the cleaning mode has exceeded a pre-determined time period is determined. If, in Step S619, the cleaning mode is determined to have not exceeded the pre-determined time period, Step S621 is performed to use the atomizer A1 to generate an aerosol at a second resonant frequency or in a second direction. The second resonant frequency is not necessarily equal to the first resonant frequency. The first direction D1 and the second direction are opposite to each other. In other words, the second resonant frequency is a variable resonant frequency, and the second resonant frequency can be higher than, equal to or lower than the first resonant frequency. The atomization device 1 enters the cleaning mode at various resonant frequencies to remove the contaminations clogging the pores on the atomizer A1. The second direction indicates the direction from the nozzle M1 to the container portion 120.

For example, in the atomization mode, the atomization device 1 provides, for example, a 5-KHz first resonant frequency to drive the atomizer A1 to provide sonic oscillation. Therefore, as time goes by, the pores on the atomizer A1 are clogged by the contaminations in the liquid. Therefore, in the cleaning mode, the atomization device 1 provides, for example, a 100 Hz-1 MHz second resonant frequency to drive the atomizer A1 to provide sonic oscillation. Therefore, the atomizer A1 increases the oscillation intensity or the oscillation frequency to remove the contaminations clogging the pores on the atomizer A1 with the use of a detergent. In brief, in the present embodiment, the resonant frequency provided by the atomization device 1 is varied to remove the contaminations clogging the pores on the atomizer A1.

If, in Step S619, the cleaning mode is determined to have exceeded the pre-determined time period, Step S623 is performed to stop the cleaning mode and turn off the host device 10. In Step S625, the atomization device 1 is turned off.

As previously stated, the present invention provides an atomization device and a cleaning method thereof. Whether the atomization device enters the cleaning mode is determined by determining whether both the container portion and the nozzle portion contain the liquid. When both the container portion and the nozzle portion contain the liquid, the atomization device enters the cleaning mode. When the container portion is determined to contain the liquid and the nozzle portion is determined to not contain the liquid, the atomization device enters the atomization mode. When the container portion is determined to not contain the liquid, the atomization device enters the safe mode. Moreover, the present invention uses an antenna in the sensor unit to sense the amount of the liquid in the jar portion non-contactly and transmits a sensed signal to the host device such that the host device determines whether to work so as to prevent the sonic oscillation circuit or the sonic oscillator in the atomization device from idling. Furthermore, in the present invention, the contaminations clogging the pores on the nozzle portion can be removed to improve convenience in the cleaning of the atomization device.

The above-mentioned descriptions represent merely the exemplary embodiment of the present invention, without any intention to limit the scope of the present invention thereto. Various equivalent changes, alterations or modifications based on the claims of the present invention are all consequently viewed as being embraced by the scope of the present invention.

What is claimed is:

1. A cleaning method for an atomization device, said atomization device comprising a jar portion and a host device, said jar portion being movably assembled with said host device, said jar portion comprising a nozzle portion and a container portion, said nozzle portion communicating with said container portion and being provided with an atomizer disposed therein, said atomizer being coupled to said host device, and said cleaning method comprising the steps of:

assembling said jar portion and said host device and turning on said host device;

determining whether said container portion contains a liquid;

entering a safe mode if said container portion is determined to not contain said liquid or determining whether said nozzle portion contains said liquid if said container portion is determined to contain said liquid; and entering an atomization mode if said nozzle portion is determined to not contain said liquid or entering a cleaning mode if said nozzle portion is determined to contain said liquid.

2. The cleaning method of claim 1, further comprising in said cleaning mode the steps of:

determining whether said cleaning mode has exceeded a pre-determined time period;

stopping said cleaning mode and turning off said host device if said cleaning mode is determined to have exceeded said pre-determined time period; or determining whether said container portion contains said liquid if said cleaning mode is determined to have not exceeded said pre-determined time period.

3. The cleaning method of claim 1, wherein the step of determining whether said container portion contains said liquid further comprises the steps of:

using a sensor unit coupled to said host device to sense whether said container portion contains said liquid;

using said sensor unit to issue a first sensed signal to said host device when said container portion contains said liquid; or using said sensor unit to issue a second sensed signal to said host device when said container portion does not contain said liquid.

4. The cleaning method of claim 1, wherein the step of determining whether said nozzle portion contains said liquid further comprises the steps of:

determining whether said nozzle portion contains said liquid according to the damping of said atomizer;

using said atomizer to issue a first frequency signal to said host device when said atomizer contains said liquid; or using said atomizer to issue a second frequency signal to said host device when said atomizer does not contain said liquid.

5. The cleaning method of claim 2, wherein the step of determining whether said nozzle portion contains said liquid further comprises the steps of:

determining whether said nozzle portion contains said liquid according to the damping of said atomizer;

using said atomizer to issue a first frequency signal to said host device when said atomizer contains said liquid; or using said atomizer to issue a second frequency signal to said host device when said atomizer does not contain said liquid.

6. The cleaning method of claim 3, wherein the step of determining whether said nozzle portion contains said liquid further comprises the steps of:

determining whether said nozzle portion contains said liquid according to the damping of said atomizer;

using said atomizer to issue a first frequency signal to said host device when said atomizer contains said liquid; or using said atomizer to issue a second frequency signal to said host device when said atomizer does not contain said liquid.

7. The cleaning method of claim 1, further comprising in said atomization mode the step of:

using said host device to output a first output power to said atomizer.

8. The cleaning method of claim 7, further comprising in said cleaning mode the step of:

using said host device to output a second output power to said atomizer, said second output power being higher than said first output power.

9. The cleaning method of claim 1, further comprising in said atomization mode the step of:

using said atomizer to generate an aerosol at a first resonant frequency or in a first direction.

10. The cleaning method of claim 9, further comprising in said cleaning mode the step of:

using said atomizer to generate an aerosol at a second resonant frequency or in a second direction, said first direction and said second direction being opposite to each other.

11. The cleaning method of claim 1, further comprising after assembling said jar portion and said host device the step of:

immersing said jar portion in said liquid.

* * * * *